(12) United States Patent
Bruna

(10) Patent No.: US 7,325,544 B2
(45) Date of Patent: Feb. 5, 2008

(54) FLUID DISPENSER DEVICE HAVING RESERVOIR WITH ADJUSTMENT MECHANISM COOPERATING WITH DEVICE BODY

(75) Inventor: Pascal Bruna, Sotteville les Rouen (FR)

(73) Assignee: Valois S.A.S., Le Neubourg (FR)

( * ) Notice: Subject to any disclaimer, the term of this patent is extended or adjusted under 35 U.S.C. 154(b) by 551 days.

(21) Appl. No.: 10/362,877

(22) PCT Filed: Aug. 28, 2001

(86) PCT No.: PCT/FR01/02682

§ 371 (c)(1),
(2), (4) Date: Sep. 10, 2003

(87) PCT Pub. No.: WO00/78378

PCT Pub. Date: Dec. 28, 2000

(65) Prior Publication Data

US 2004/0025868 A1 Feb. 12, 2004

(30) Foreign Application Priority Data

Aug. 29, 2000 (FR) .................................. 00 11009

(51) Int. Cl.
*A61M 11/00* (2006.01)
(52) U.S. Cl. .............................. 128/200.23; 128/203.19

(58) Field of Classification Search ........... 128/200.23, 128/203.15, 203.19; 222/163, 325, 402.1, 222/402.13, 402.2
See application file for complete search history.

(56) References Cited

U.S. PATENT DOCUMENTS

| 3,157,317 A | 11/1964 | Ramsbotham |
| 3,662,958 A | 5/1972 | German |
| 5,387,034 A | 2/1995 | Bauer et al. |
| 5,904,139 A * | 5/1999 | Hauser .................. 128/200.23 |

FOREIGN PATENT DOCUMENTS

WO WO 00/78378 A1 12/2000

\* cited by examiner

*Primary Examiner*—Steven O. Douglas
(74) *Attorney, Agent, or Firm*—Sughrue Mion, PLLC

(57) ABSTRACT

A fluid dispenser device comprising a fluid reservoir (10), and a dispensing member (20), such as a metering valve, fitted to said reservoir (10), said reservoir (10) and said valve (20) being assembled into a body (30) incorporating a dispensing orifice (31), said device being characterized in that it includes an adjustment element (40) disposed between the reservoir (10) and the body (30), said adjustment element (40) being provided with adapter means (45) that are movable and/or deformable and that co-operate with the body (30) and/or with the reservoir (10) while the reservoir (10) is being assembled into the body (30), thereby compensating for the manufacturing tolerances of said body (30) and/or of said reservoir and/or said dispensing member (20).

18 Claims, 2 Drawing Sheets

FLUID DISPENSER DEVICE HAVING RESERVOIR WITH ADJUSTMENT MECHANISM COOPERATING WITH DEVICE BODY

BACKGROUND OF THE INVENTION

1. Field of the Invention

The present invention relates to a fluid dispenser device, and more particularly to an improved fluid inhaler.

2. Description of Related Art

In certain types of fluid dispenser device, and in particular devices of the aerosol type, including a metering valve adapted to dispense a substance contained in a reservoir by means of a propellant gas, the unit formed by the metering valve and by the reservoir is generally assembled into a body which incorporates a mouthpiece or a nasal applicator, and which facilitates handling of the device. In certain cases, said body may also include an inhalation-driven trigger device which co-ordinates actuation of the metering valve with inhalation of patient. In this type of device, the problem arises of compensating for manufacturing tolerance, at the body, at the reservoir, or at the metering valve, in order to avoid poor-quality assembly which could prevent the valve from operating reliably. More particularly, in a device including an inhalation-driven actuating system, the unit formed by the reservoir and by the metering valve must be assembled into the body very accurately so as to enable the inhalation-driven actuating system to co-operate reliably with the said metering valve. One way of compensating for manufacturing tolerances is to act on the travel stroke of the valve member, but that is not acceptable when the metered quantities or "doses" to be dispensed must be accurately reproducible. In addition, assembly in which a certain amount of clearance exists between the various components can also prevent the device from operating safely and reliably, which is not acceptable.

Document U.S. Pat. No. 5,904,139 discloses cone-on-cone snug interfitting between a bottom portion of the body that is provided with the mouthpiece, and the top portion of the body that contains the reservoir. The depth of the interfitting can be varied slightly to compensate for the manufacturing tolerances, deeper interfitting inducing radial forces between the two portions of the body.

Document U.S. Pat. No. 3,157,317 discloses a deformable elastomer element disposed between the bottom of the reservoir and the body of the inhaler so as to compensate for the manufacturing tolerances. If that element is deformed it exerts an axial force on the reservoir and on the body.

SUMMARY OF THE INVENTION

An object of the present invention is to provide a fluid dispenser device that does not suffer from the above-mentioned drawbacks.

An object of the present invention is thus to provide a fluid dispenser device that guarantees that the body and the dispensing member of the reservoir are assembled together accurately, independently of the manufacturing tolerances of the three elements, and without inducing compression or deformation forces between said elements.

Another object of the present invention is to provide a fluid dispenser device that is simple and inexpensive to manufacture and to assemble.

Yet another object of the present invention is to provide a fluid dispenser device that is actuated by inhalation, and that enables the dispensing member to be separated from the inhalation-driven actuating system so as to enable said dispensing member to be actuated manually.

The present invention therefore provides a fluid dispenser device comprising a fluid reservoir, and a dispensing member, such as a metering valve, fitted to said reservoir, said reservoir and said valve being assembled into a body incorporating a dispensing orifice, said device being characterized in that it includes an adjustment element disposed between the reservoir and the body, said adjustment element being provided with adapter means that are movable and/or deformable and that cooperate with the body and/or with the reservoir while the reservoir is being assembled into the body, thereby compensating for the manufacturing tolerances of said body and/or of said reservoir and/or said dispensing member.

Advantageously, once the fluid dispenser device has been assembled, said adjustment element exerts substantially no force on the reservoir, on the body, and/or on the dispensing member.

Advantageously, said adjustment element is provided with axial openings, and the adapter means are implemented in the form of small cylinders that can slide snugly in said openings while said reservoir is being assembled into the body.

Advantageously, prior to assembly, said small cylinders are fixed to said openings by bridges of material that are deformable and/or breakable.

Preferably, said adjustment element is fixed to the bottom of the reservoir and is fitted to the body while said reservoir is being assembled into said body.

Advantageously, the adjustment element is fitted to the body removably.

Advantageously, the adjustment element is fitted to the body by turning e.g. through one fourth of a turn.

Advantageously, the device includes an inhalation-driven trigger system for triggering the dispensing member, actuation of said dispensing member being separated from said inhalation-driven trigger system when said adjustment element is disassembled from said body, thereby enabling said dispensing member to be actuated manually.

BRIEF DESCRIPTION OF THE DRAWINGS

Other characteristics and advantages of the present invention will appear more clearly on reading the following detailed description given by way of non-limiting example, and with reference to the accompanying drawings, in which.

DETAILED DESCRIPTION OF ILLUSTRATIVE, NON-LIMITING EMBODIMENTS OF THE INVENTION

The present invention is described below with reference to an embodiment in which the fluid dispenser device is an inhaler having a metering valve, and generally operating in the upside-down position. However, the invention is not limited to this type of device. Rather, it is applicable to all fluid dispenser devices in which manufacturing tolerance problems can arise during assembly at the body, at the reservoir, or at the dispensing element.

Figure 1:
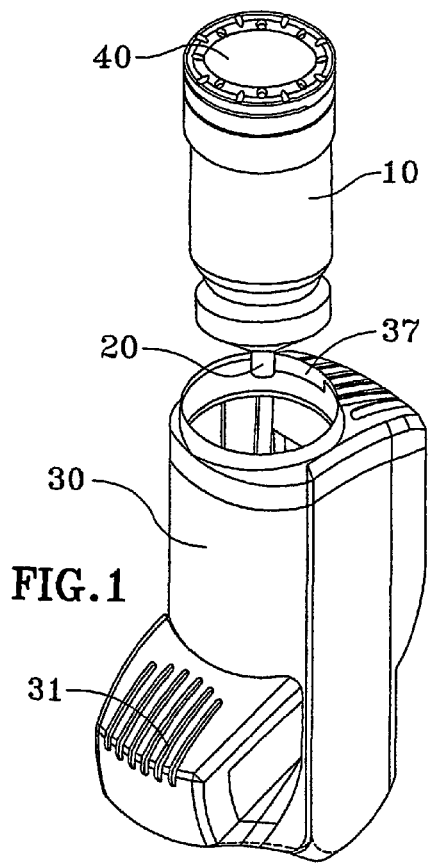
FIG. 1 is a diagrammatic perspective view of a device in an advantageous embodiment of the invention, before the reservoir is assembled into the body.
Figure 2:
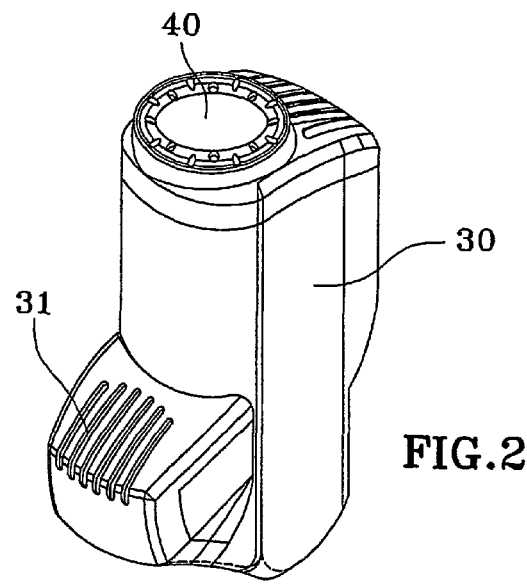
FIG. 2 is a view similar to FIG. 1, after the reservoir has been assembled into the body.

With reference to FIGS. 1 and 2, the dispenser device includes a reservoir 10 to which a dispensing member 20, which is a metering valve in this example, is fixed by means of a fixing ring, which is a crimped cap in this example. The resulting unit formed of the reservoir 10 and of the metering valve 20 is then assembled into a body 30 incorporating a dispensing orifice 31, which, in this example, is implemented in the form of a mouthpiece. It should be noted that, in the example shown in FIGS. 1 and 2, the mouthpiece is covered with a cover, but said cover has no repercussions on the present invention.

Figure 7:
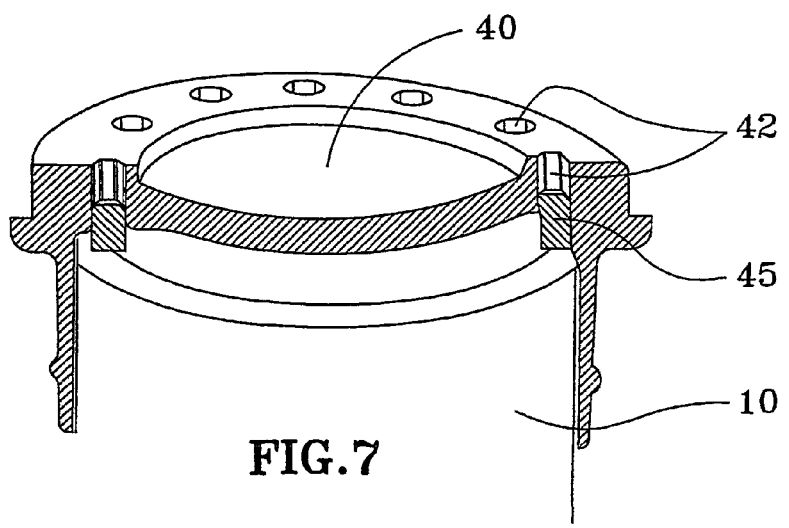
FIG. 7 is a diagrammatic view of the adjustment element in an advantageous embodiment of the present invention.

In the invention, the device includes an adjustment element 40 which is disposed between the reservoir 10 and the body 30. For example, the adjustment element 40 may be implemented in the form of a ring which is fixed to the bottom of the reservoir 10, as shown more clearly in FIGS. 3, 4 and 7. The adjustment element 40 may be fixed to the reservoir 10 in any manner, e.g. by snap-fastening or the like.

Figure 3:
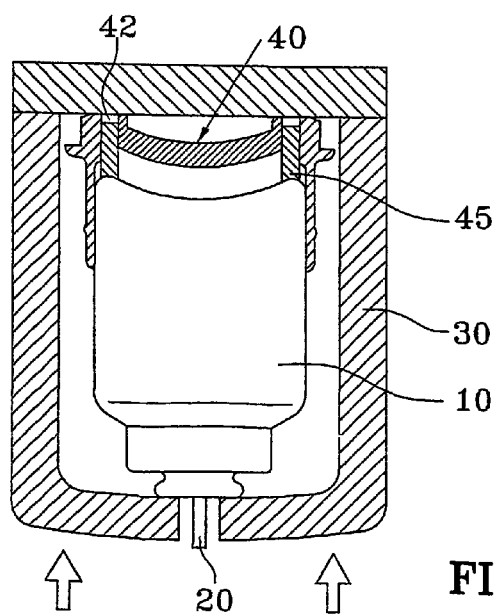
FIG. 3 is a diagrammatic cross-section view of said device as assembled, in an advantageous embodiment of the present invention.
Figure 4:
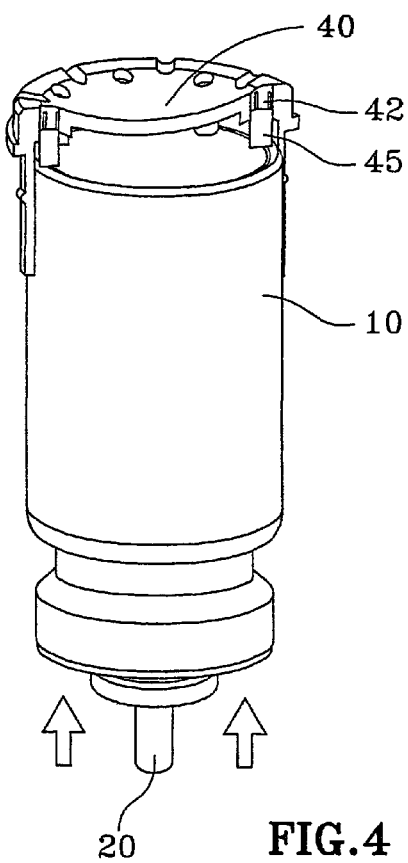
FIG. 4 is a partially cut-away diagrammatic view of the device in an advantageous embodiment of the present invention.
Figure 5:
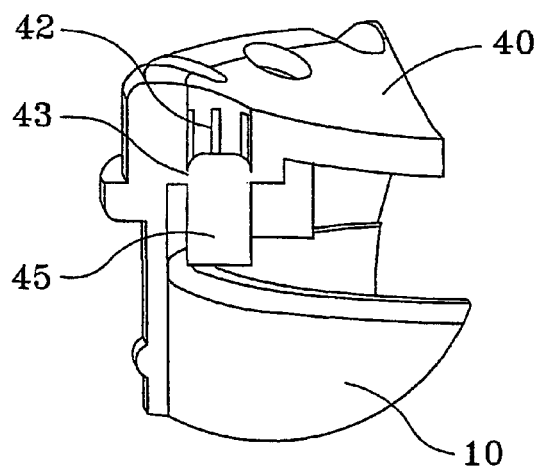
FIGS. 5 and 6 are diagrammatic detail views of the adapter means in an advantageous embodiment of the present invention, respectively before and after the reservoir is assembled into the body.
Figure 6:
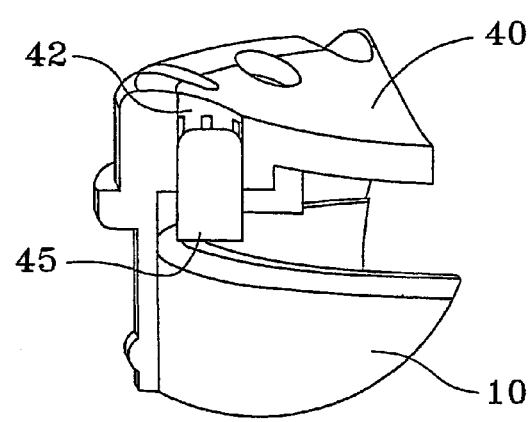

The adjustment element 40 is provided with adapter means 45 which are movable and/or deformable and which co-operate with the body 30 and/or with the reservoir 10 while said reservoir 10 is being assembled into said body 30. Thus, while the device is being assembled, this makes it possible to compensate for any manufacturing tolerance at said body, at said reservoir and/or at said dispensing member, in particular at the valve member thereof. As shown more clearly in FIGS. 3, 4, 5, 6, and 7, said adapter means may be implemented in the form of small cylinders 45 which can slide snugly inside respective openings 42 disposed axially inside the adjustment element 40. With reference to FIG. 5, which shows the reservoir 10 prior to being finally assembled into the body 30, the adjustment element 40 is pre-positioned on and, in this example, fixed to the reservoir 10, and the small cylinders 45 are not urged by said reservoir into said respective openings 42. While the unit formed by the body 10 and by the metering valve 20 is being assembled into the body 30, which is shown more clearly in FIGS. 3 and 4, an axial force in the direction indicated by the arrows shown in FIGS. 3 and 4 is exerted by the bottom of the reservoir 10 on said small cylinders 45. Said cylinders then slide snugly inside said axial openings 42 until assembly is finished, thereby taking up any slack between the body 30 and the metering valve, between the reservoir 10 and the adjustment element 40, and between the adjustment element 40 and the body 30. Advantageously, as shown in FIG. 3, the small cylinders 45 may, prior to assembly, be fixed to said openings 42 by bridges of material 43 that are deformable and/or breakable.

Advantageously, as shown in FIG. 1, the adjustment element 40 is fixed to the bottom of the reservoir 10 and is then fitted to the body 30 while said reservoir 10 is being assembled into the body 30. More precisely, the adjustment element may be fitted to be removable, e.g. by being turned through one fourth of a turn, as represented diagrammatically in FIG. 1 by the groove 37 provided for this purpose inside the opening in the body 30, which groove co-operates with said adjustment element 40. This implementation is particularly advantageous in an inhaler device triggered by the user inhaling. In which case, the device (generally referred to as a "Metered Dose Inhaler" or "MDI") includes a system for actuating the metering valve by means of the patient inhaling, which system is coupled to said metering valve. However, it is sometimes desirable, in certain special cases, for the metering valve to be actuated manually. This is generally not possible, or else it is very complicated without completely disassembling the device. With the present invention, the metering valve 20 can be released from the inhalation-driven trigger system very simply merely by disassembling the adjustment element 40 from said body 30. In which case, the bottom of the reservoir becomes accessible to the user who can then manually actuate the metering valve by exerting axial pressure on it. The inhalation-driven trigger system is not shown in the drawings, but it is well known to the person skilled in the art that such systems, which are well known and described in the prior art, co-operate with the valve member of the metering valve 20. By disassembling the adjustment element 40 from the body 30, it is possible to release said valve member temporarily from the inhalation-driven trigger system, and thus to actuate said metering valve manually.

Naturally, the invention is described above merely with reference to very diagrammatic drawings, and clearly modifications may be made to it without going beyond the ambit of the present invention as defined by the accompanying drawings. In particular, the adapter means are not necessarily implemented in the form of small cylinders, and they may take any suitable form making it possible to compensate axially for the manufacturing tolerances of the various elements to be assembled together in a fluid dispenser device.

The invention claimed is:

1. A fluid dispenser device comprising a fluid reservoir (10), and a metering valve (20), fitted to said reservoir (10), said reservoir (10) and said valve (20) being assembled into a body (30) incorporating a dispensing orifice (31), said device being characterized in that it includes an adjustment element (40) disposed between the reservoir (10) and the body (30), said adjustment element (40) including adapter means (45) that are movable or deformable and that co-operate with the body (30) or with the reservoir (10) while the reservoir (10) is being assembled into the body (30), thereby compensating for the manufacturing tolerances of said body (30) or of said reservoir or said valve (20), said adjustment element exerting substantially no force on the reservoir (10), on the body (30), or on the valve (20), once the fluid dispenser device has been assembled.

2. A device according to claim 1, in which the adjustment element (40) is provided with axial openings (42), and the adapter means are implemented in the form of small cylinders (45) that can slide snugly in said openings (42) while said reservoir (10) is being assembled into the body (30).

3. A device according to claim 2, in which, prior to assembly, said small cylinders (45) are fixed to said openings (42) by bridges of material (43) that are deformable or breakable.

4. A device according to claim 1, in which said adjustment element (40) is fixed to the bottom of the reservoir (10) and is fitted to the body (30) while said reservoir (10) is being assembled into said body (30).

5. A device according to claim 4, in which the adjustment element (40) is removably fitted to the body (30).

6. A device according to claim 5, in which the adjustment element (40) is fitted to the body (30) by turning.

7. A device according to claim 5, in which the device includes an inhalation-driven trigger system for triggering the valve (20), actuation of said value (20) being separated from said inhalation-driven trigger system when said adjustment element (40) is disassembled from said body (30), thereby enabling said valve (20) to be actuated manually.

8. The device according to claim 1, wherein the adapter means is structured to be slidable within the adjustment element simultaneously during assembly so as to eliminate slack between one or more of the body and the valve, the reservoir and the adjustment element, and the adjustment element and the body.

9. A fluid dispenser device comprising:
a body comprising a dispensing orifice,
a fluid reservoir,
a valve, and
a length adjustment mechanism coupled to the reservoir; and
wherein the reservoir, the length adjustment mechanism, and the valve are assembled in the body with the length adjustment mechanism disposed between the reservoir and the body; and
wherein the length adjustment mechanism is structured to cooperate with the body such that, as the reservoir, the length adjustment mechanism, and the valve are assembled in the body, the length adjustment mechanism changes in axial length to compensate for manufacturing tolerances in one or more of the body, reservoir and valve so as to eliminate slack between one or more of the body and the valve, the reservoir and the length adjustment element, and the length adjustment element and the body, and without the length adjustment mechanism applying a substantial force on the body after the reservoir and valve are finally assembled in the body.

10. The device according to claim 9, wherein the length adjustment mechanism comprises at least one element snugly fit within an axial opening located in the length adjustment mechanism and wherein the element is axially slidable within the opening and relative to the reservoir and valve so as to adjust the combined length of the reservoir, the length adjustment mechanism, and the valve.

11. The device according to claim 10, further comprising a plurality of elements and corresponding openings.

12. The device according to claim 10, wherein the element is a cylindrical structure.

13. The device according to claim 9, wherein the length adjustment mechanism is coupled to an end of the reservoir that is opposite an end having the valve.

14. The device according to claim 1, wherein the adjustment element exerts substantially no force on the reservoir, substantially no force on the body and substantially no force on the valve, once the fluid dispenser device has been assembled.

15. The device according to claim 9, wherein the length adjustment mechanism is disposed axially between the reservoir and the body.

16. The device according to claim 1, wherein the adjustment element comprises at least one axially moveable or deformable adapter element held by friction within a corresponding opening in the adjustment element and wherein the adapter element cooperates with the reservoir during assembly in the body so that the adapter element is axially pushed within the corresponding opening.

17. A fluid dispenser device comprising:
a body comprising a dispensing orifice,
a fluid reservoir,
a valve, and
a length adjustment mechanism coupled to the reservoir; and
wherein the reservoir, the length adjustment mechanism, and the valve are assembled in the body with the length adjustment mechanism disposed between the reservoir and the body; and
wherein the length adjustment mechanism is structured to cooperate with the body such that, as the reservoir, the length adjustment mechanism, and the valve are assembled in the body, the length adjustment mechanism changes in axial length to compensate for manufacturing tolerances in one or more of the body, reservoir and valve so as to eliminate slack between one or more of the body and the valve, the reservoir and the length adjustment element, and the length adjustment element and the body, and without the length adjustment mechanism inducing compression or deformation forces between the body and the reservoir or the valve after the reservoir and valve are finally assembled in the body.

18. The device according to claim 17, wherein the length adjustment mechanism comprises at least one element snugly fit within an axial opening located in the length adjustment mechanism and wherein the element is axially slidable within the opening and relative to the reservoir and valve so as to adjust the combined length of the reservoir, the length adjustment mechanism, and the valve.

* * * * *